US010449139B2

(12) United States Patent
Pimenta et al.

(10) Patent No.: US 10,449,139 B2
(45) Date of Patent: *Oct. 22, 2019

(54) AQUEOUS ORAL CARE COMPOSITIONS

(75) Inventors: Paloma Pimenta, Staten Island, NY (US); Marilou T. Joziak, South River, NJ (US); Edward Joziak, legal representative, Monroe Township, NJ (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 408 days.

This patent is subject to a terminal disclaimer.

(21) Appl. No.: 13/997,381

(22) PCT Filed: Dec. 23, 2010

(86) PCT No.: PCT/US2010/061959
§ 371 (c)(1),
(2), (4) Date: Jun. 24, 2013

(87) PCT Pub. No.: WO2012/087325
PCT Pub. Date: Jun. 28, 2012

(65) Prior Publication Data
US 2013/0272971 A1    Oct. 17, 2013

(51) Int. Cl.
A61K 31/723    (2006.01)
A61K 31/78     (2006.01)
A61Q 11/00     (2006.01)
A61K 8/73      (2006.01)
A61K 8/81      (2006.01)

(52) U.S. Cl.
CPC .............. *A61K 8/731* (2013.01); *A61K 8/73* (2013.01); *A61K 8/8147* (2013.01); *A61Q 11/00* (2013.01); *A61K 2800/594* (2013.01)

(58) Field of Classification Search
CPC ...... A61Q 11/00; A61K 8/8147; A61K 8/731; A61K 8/736; A61K 8/73; A61K 31/79; A61K 8/8176; A61K 8/8182
See application file for complete search history.

(56) References Cited

U.S. PATENT DOCUMENTS

| | | | |
|---|---|---|---|
| 3,943,063 A | 3/1976 | Morishita et al. | |
| 5,015,467 A * | 5/1991 | Smitherman | A61K 8/19 424/435 |
| 5,137,729 A | 8/1992 | Kuroya et al. | |
| 5,202,112 A * | 4/1993 | Prencipe | A61Q 11/00 424/49 |
| 5,334,375 A | 8/1994 | Nabi et al. | |
| 5,562,939 A | 10/1996 | Lewis | |
| 5,658,554 A * | 8/1997 | Fisher | A61K 33/42 424/49 |
| 5,776,435 A | 7/1998 | Gaffar et al. | |
| 5,876,744 A * | 3/1999 | Della Valle | A61K 8/732 424/434 |
| 6,106,883 A | 8/2000 | Sokolik et al. | |
| 6,153,210 A | 11/2000 | Roberts et al. | |
| 6,159,459 A * | 12/2000 | Hunter et al. | 424/78.08 |
| 6,595,997 B2 | 7/2003 | Axelson, Jr. et al. | |
| 6,596,298 B2 | 7/2003 | Leung et al. | |
| 6,602,841 B1 | 8/2003 | Becker et al. | |
| 6,682,721 B2 | 1/2004 | Kim et al. | |
| 6,683,067 B2 | 1/2004 | Lawler et al. | |
| 7,008,979 B2 | 3/2006 | Schottman et al. | |
| 7,241,411 B2 | 7/2007 | Berry et al. | |
| 7,357,891 B2 | 4/2008 | Yang et al. | |
| 7,723,430 B2 | 5/2010 | Kunitake et al. | |
| 2001/0006624 A1 | 7/2001 | Witt et al. | |
| 2002/0041852 A1 | 4/2002 | Napolitano et al. | |
| 2002/0192350 A1* | 12/2002 | Hynes | A23L 2/02 426/590 |
| 2003/0060486 A1* | 3/2003 | Jacob | A61K 9/006 514/320 |
| 2003/0215401 A1 | 11/2003 | Estrada et al. | |
| 2005/0214720 A1* | 9/2005 | Milanovich | A61K 8/22 433/215 |
| 2006/0110416 A1 | 5/2006 | Ryles et al. | |
| 2007/0044824 A1 | 3/2007 | Capeci et al. | |
| 2007/0053849 A1 | 3/2007 | Doyle et al. | |
| 2007/0059257 A1* | 3/2007 | Estrada | A61K 8/0216 424/52 |
| 2007/0122358 A1 | 5/2007 | Wang et al. | |
| 2007/0122359 A1* | 5/2007 | Wang et al. | 424/52 |
| 2008/0317703 A1* | 12/2008 | Kawa et al. | 424/78.32 |
| 2009/0068122 A1 | 3/2009 | Pilch et al. | |
| 2009/0068259 A1 | 3/2009 | Pilch et al. | |
| 2009/0238777 A1 | 9/2009 | Joziak et al. | |
| 2010/0076080 A1 | 3/2010 | Yelm et al. | |

(Continued)

FOREIGN PATENT DOCUMENTS

JP    2002-226315    8/2002
JP    2005-187330    7/2005

(Continued)

OTHER PUBLICATIONS

Johanson, Pharmaceutical Manufacturing International, (1995) pp. 1-4.*
Todica et al. Chinese Physics Letters, 27(1), (2010).*
Mehravaran et al., Iranian Journal of Pharmaceutical Research, 8: 3-13 (2009).*
Speers et al., Journal of Food Science, 51: 96-98 (1986).*
Abdelrahim et al., International Journal of Food Science and Technology, 29: 243-253 (1994).*
E3070—16, ASTM, accessed at https://compass.astm.org/download/E3070.10291.pdf downloaded May 16, 2017.*
Pereira et al., B. Ceppa, 25(2), pp. 285-294. (Year: 2007).*
Marcotte et al., Journal of Food Engineering, 48, pp. 157-167. (Year: 2001).*

(Continued)

*Primary Examiner* — Abigail Vanhorn

(57) ABSTRACT

Described herein are aqueous compositions comprising polymers, which deliver a polymer film to surfaces of the oral cavity to relieve dry mouth; and methods of preparing and using the same.

10 Claims, No Drawings

(56) References Cited

U.S. PATENT DOCUMENTS

| | | |
|---|---|---|
| 2010/0247644 A1 | 9/2010 | Domb et al. |
| 2011/0189110 A1 | 8/2011 | Kohli et al. |
| 2014/0305461 A1* | 10/2014 | Pimenta .................. A61K 8/44 132/200 |

FOREIGN PATENT DOCUMENTS

| | | |
|---|---|---|
| JP | 2009-084279 | 4/2009 |
| RU | 2248787 | 3/2005 |
| WO | WO 95/20971 | 8/1995 |
| WO | WO 02/022096 | 3/2002 |
| WO | WO 06/013081 | 2/2006 |
| WO | WO 12/087324 | 6/2012 |
| WO | WO 12/087326 | 6/2012 |
| WO | WO 12/087327 | 6/2012 |
| WO | WO 12/087328 | 6/2012 |

OTHER PUBLICATIONS

Corcoran et al., 2006, "Evaluation of a combined polymer system for use in relieving the symptoms of xerostomia," J. Clinical Dentistry 17(2):34-38.

International Search Report and Written Opinion in International Application No. PCT/US2010//061959, dated Oct. 13, 2011.

Preetha et al., 2005, "Comparison of Artificial Saliva Substitutes," Trends Biomater. Artificial Organs 18(2):178-186.

Urquhart et al., 2006, "Review of the use of polymers in saliva substitutes for symptomatic relief of xerostomia," J. Clinical Dentistry 17(2):29-33.

Van Der Reijden et al., 1994, "Rheological properties of commercially available polysaccharides with potential use in saliva substitutes," Biorheology 31(6):631-642.

Van Der Redden et al., 1996, "Treatment of xerostomia with polymer-based saliva substitutes in patients with Sjögren's syndrome," Arthritis and Rheumatology 39(1):57-63.

* cited by examiner

AQUEOUS ORAL CARE COMPOSITIONS

BACKGROUND

Dry mouth may be caused by several different factors including but not limited genetics, systemic illness, reactions to medications and aging. The degree to which an individual can experiences dry mouth can vary greatly. Stimulation of saliva production and use of oral moisturizers and substitute saliva are used to reduce dry mouth. Saliva production may be stimulated by various modalities such as mechanical, chemical, electrical and pharmacological. Of the products commercially available, the degree and duration of effectiveness varies. Thus, there is a need for more effective, longer lasting compositions that can be used to moisten the oral cavity and reduce dry mouth in individuals.

SUMMARY

Some embodiments of the present invention provide compositions that comprise a blend of polymers in proportions which form a viscoelastic polymer network with specific desirable rheological characteristics. In some embodiments, the composition delivers the polymer network to an oral cavity surface, which in turn serves as a mucoadhesive polymer film within the oral cavity, providing a coating that restores moisture and lubricity similar to that provided by natural saliva. In some embodiments, the polymer film binds water and provides relieves the feeling of dry mouth.

Some embodiments provide aqueous oral care compositions comprising: a gum-type colloidal polymer; a cellulosic polymer; an acrylate polymer; and an orally acceptable aqueous carrier. In some embodiments, the gum-type colloidal polymer is xanthan gum. In some embodiments, the cellulosic polymer is cellulose gum. In some embodiments, the acrylate polymer is carbomer. Some embodiments provide an aqueous oral care composition comprising: xanthan gum; cellulose gum; carbomer; and an orally acceptable aqueous carrier. Still other embodiments provide methods of treating or preventing a disease or condition of the oral cavity comprising contacting an oral cavity surface of a subject in need thereof, with any one of the compositions described herein.

DETAILED DESCRIPTION

As used throughout, ranges are used as shorthand for describing each and every value that is within the range. Any value within the range can be selected as the terminus of the range.

All references cited herein are hereby incorporated by reference in their entireties.

In the event of a conflict in a definition in the present disclosure and that of a cited reference, the present disclosure controls.

As used herein, the term "viscoelastic fluid" refers to a complex fluid that exhibits mechanical properties that are both elastic (solid-like e.g. rubber) and viscous (liquid-like, flowable e.g. water). A viscoelastic fluid composition will deform and flow under the influence of an applied shear stress (e.g. shaking or swishing in the mouth), but when the stress is removed the composition will recover from the deformation. The elastic portion of the viscoelastic behavior is quantified by the elastic modulus (G'), while the viscous portion is quantified by the viscous modulus (G").

As used herein, the term "shear thinning" refers to a property in which viscosity decreases with increasing rate of shear stress. Materials that exhibit shear thinning properties are called pseudoplastic.

As used herein, "structured fluid" and "structured composition" may be used interchangeably, and refer to a fluid that exhibits a G' value greater than the G" value (i.e. the ratio of G' to G" is >1) within the linear viscoelastic region of a strain sweep measurement. The ratio of G' to G" has been identified as the Structural Parameter.

Some embodiments provide aqueous oral care compositions comprising: a gum-type colloidal polymer; a cellulosic polymer; an acrylate polymer; and an orally acceptable aqueous carrier. In some embodiments, the gum-type colloidal polymer is xanthan gum. In some embodiments, the cellulosic polymer is cellulose gum. In some embodiments, the acrylate polymer is carbomer.

Some embodiments of the present invention provide aqueous oral care compositions comprising: xanthan gum; cellulose gum; carbomer; and an orally acceptable aqueous carrier. In some embodiments the compositions comprise: from about 0.01 to about 0.5%, by weight, xanthan gum; from about 0.01 to about 0.5%, by weight, cellulose gum; and from about 0.01 to about 0.5%, by weight, carbomer.

As used herein, the term "aqueous" refers to a free water content of at least about 40%, by weight.

In some embodiments, the compositions comprise from about 40 to about 97%, by weight, free water. In some embodiments, the compositions comprise greater than about 50%, by weight, free water. In some embodiments, the compositions comprise from about 50 to about 90%, by weight, free water. In some embodiments, the compositions comprise from about 60 to about 80%, by weight, free water. In some embodiments, the compositions comprise about 70%, by weight, free water. Some embodiments comprise about 70%, about 71%, about 72%, about 73%, about 74% or about 75%, by weight, free water.

Some embodiments provide compositions comprising: from about 0.05 to about 0.1%, by weight, xanthan gum. Further embodiments provide compositions comprising from about 0.05 to about 0.1%, by weight, cellulose gum. Other embodiments provide compositions comprising from about 0.03 to about 0.1%, by weight, carbomer.

Some embodiments provide compositions comprising: from about 0.05 to about 0.1%, by weight, xanthan gum; from about 0.05 to about 0.1%, by weight, cellulose gum; and from about 0.03 to about 0.1%, by weight, carbomer.

Some embodiments provide compositions comprising: from about 0.07 to about 0.09%, by weight, xanthan gum. Further embodiments provide compositions comprising from about 0.07 to about 0.09%, by weight, cellulose gum. Other embodiments provide compositions comprising from about 0.04 to about 0.06%, by weight, carbomer.

In some embodiments, the compositions comprise: from about 0.07 to about 0.09%, by weight, xanthan gum; from about 0.07 to about 0.09%, by weight, cellulose gum; and from about 0.04 to about 0.06%, by weight, carbomer.

Some embodiments provide compositions comprising: about 0.08%, by weight, xanthan gum. Further embodiments provide compositions comprising about 0.08%, by weight, cellulose gum. Other embodiments provide compositions comprising from about 0.05%, by weight, carbomer.

Still further embodiments provide compositions comprising: about 0.08%, by weight, xanthan gum; about 0.08%, by weight, cellulose gum; and about 0.05%, by weight, carbomer. Yet other embodiments provide compositions comprising: 0.083%, by weight xanthan gum; 0.083%, by weight, cellulose gum; 0.05%, by weight, carbomer.

In some embodiments, the compositions further comprise an antibacterial agent. In some embodiments, the antibacterial agent is cetylpyridinium chloride.

Some embodiments provide compositions further comprising a humectant. Other embodiments provide compositions comprising a humectant selected from: glycerin; sorbitol; ethanol; propylene glycol; and a combination of two or more thereof.

In some embodiments the compositions further comprise one or more components selected from a fluoride ion source; a tartar control agent; a buffering agent; an abrasive; and a combination of two or more thereof. In some embodiments, at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

In some embodiments, the composition is a mouthwash or mouthrinse.

In some embodiments, the compositions have a Flow Rate Index less than 1. In other embodiments, the compositions have a Flow Rate Index from about 0.1 to about 0.8. Still other embodiments provide compositions having a Flow Rate Index from about 0.3 to about 0.6. Yet other embodiments provide compositions having a Flow Rate Index of about 0.5.

Some embodiments of the present invention provide compositions having a Consistency Index greater than 10. Other embodiments provide compositions having a Consistency Index greater than 100. Further embodiments of the present invention provide compositions having a Consistency Index greater than 150. Still other embodiments provide compositions having a Consistency Index greater than 160. While other embodiments provide compositions having a Consistency Index of about 163.

Some embodiments provide methods of treating or preventing a disease or condition of the oral cavity comprising contacting an oral cavity surface of a subject in need thereof, with any one of the compositions described herein. In some embodiments, the disease or condition of the oral cavity is xerostomia.

In some embodiments, the composition is a mouthrinse or mouthwash. In some embodiments, the composition comprises a blend of polymers which form the polymer network that are viscoelastic in nature. In other embodiments, the polymer network has viscous characteristics and elastic characteristics which make it particularly useful when used in an aqueous composition. In some embodiments, the compositions exhibit shear thinning behavior when used. Under the stress applied to the liquid in the ordinary use of the compositions, the viscosity of the composition decreases, resulting in a more freely flowing solution which provides a wide coverage of the entire oral cavity when used. In some embodiments, the viscosity of the compositions is relatively high.

In some embodiments, use of the composition results in delivery of a film that coats both the hard and soft tissue of the oral cavity, thereby promoting lubrication, restoring moisture and providing a pleasant mouthfeel. The shear thinning properties of the compositions are similar to those of saliva.

Cellulose gum is a cellulose derivative. Cellulose derivative polymers such as cellulose gum may be of any length or combination of lengths.

Synthetic high molecular weight polymers of acrylic acid known as carbomer may be homopolymers of acrylic acid, crosslinked with an allyl ether pentaerythritol, allyl ether of sucrose or allyl ether of propylene. Carbomer has a USP classification of "carbomer homopolymer Type A". Carbomers have the ability to adsorb, retain water and swell to many times their original volume. Carbomers codes (910, 934, 940, 941, 971, 974 and 934P) are an indication of molecular weight and the specific components of the polymer.

In some embodiments, the combination of polymers in the composition imparts upon the product desirable viscoelastic properties. The shear thinning behavior of the compositions may be quantified in terms of Flow Rate Index ("n"). The Flow Rate Index of water equals 1. Against this standard, the Flow Rate Index of shear thinning liquids is less than 1.

The overall viscosity index, which is referred to as the Consistency Index ("k") of the compositions is typically high, for example about two orders of magnitude greater than water. Accordingly, the Flow Rate Index is typically low, such as less than 1, and the Consistency Index is typically high, e.g. greater than 10. The combination of a Flow Rate Index of less than 1, and Consistency Index of greater than 10, is responsible, in part, for the desirable characteristics provided by compositions described herein.

In some embodiments, the composition is substantially liquid in character, i.e. a mouthwash or oral rinse. In some embodiments, the carrier is predominantly made up of free water, i.e. an aqueous solution. In some embodiments, one or more of water, sorbitol, glycerin and propylene glycol comprise at least about 80%, by weight, of the composition. In some embodiments, one or more of water, sorbitol, glycerin and propylene glycol comprise at least about 90%, by weight, of the composition.

Humectants useful herein include polyhydric alcohols such as glycerin, sorbitol, xylitol or low molecular weight PEGs, alkylene glycol such as polyethylene glycol or propylene glycol. In various embodiments, humectants are operable to prevent hardening of paste or gel compositions upon exposure to air. In various embodiments humectants also function as sweeteners.

In some embodiments, the humectant is present in the amount of about 1 to about 40% each by weight. In some embodiments, the humectant is sorbitol. In some embodiments sorbitol present at a concentration of from about 5 to about 25%, by weight. In some embodiments sorbitol present at a concentration of from about 5 to about 15%, by weight. In some embodiments, the sorbitol is present at a concentration of about 10%, by weight. Reference to sorbitol herein refers to the material typically as available commercially in 70% aqueous solutions. In some embodiments, the total humectant concentration is from about 1 to about 60%, by weight.

In some embodiments, the humectant is glycerin. In some embodiments, glycerin is present at a concentration of from about 5 to about 15%, by weight. In some embodiments, glycerin present is at a concentration of about 7.5%, by weight.

In some embodiments, the humectant is propylene glycol. In some embodiments, propylene glycol is present at a concentration of about 5 to about 15%, by weight. In some embodiments, propylene glycol is present at a concentration of about 7%, by weight.

Other examples of humectants include ethylene glycol, dipropylene glycol, hexylene glycol, methyl cellosolve, ethyl cellosolve, vegetable oils and waxes containing at least about 12 carbons in a straight chain such as olive oil, castor oil and petrolatum and esters such as amyl acetate, ethyl acetate and benzyl benzoate.

One or more humectants may be present in a total amount of about 1% to about 50%, for example about 2% to about 45% or about 5% to about 35%, or about 10% to about 25%, by weight.

Other optional additives may be included. Among such optional additives, included are those provided in order to change appearance or aesthetic appeal, and/or to preserve the final product, and/or for taste/cosmetic appeal and/or as therapeutic and prophylactic ingredients for oral health, prevention or treatment of a condition or disorder of hard or soft tissue of the oral cavity, or the prevention or treatment of a physiological disorder or condition.

Some embodiments provide a composition wherein a preservative is present. In some embodiments, the preservative is selected from parabens, potassium sorbate, benzyl alcohol, phenoxyethanol, polyaminopropryl biguanide, caprylic acid, sodium benzoate and cetylpyridinium chloride. In some embodiments, the preservative is present at a concentration of from about 0.0001 to about 1%, by weight. In some embodiments, the preservative is present at a concentration of from about 0.01 to about 1%, by weight. In some embodiments, the preservative is present at a concentration of about 0.5%, by weight.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-n-aphthalenesulfonic acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sul-fophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-.DELTA.-3,5-cycl-ohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Flavor agents are known, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used. Typically, flavorants if included are present at 0.01-1%, by weight. In some embodiments, flavoring may be present in about 0.2%, by weight.

Sweeteners include both natural and artificial sweeteners. Suitable sweetener include water soluble sweetening agents such as monosaccharides, disaccharides and poysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be about 0.001% to about 5% by weight of the composition. In some embodiments, the sweetener is sodium saccharin and present at about 0.01% by weight of the composition.

Optional breath freshening agents may be provided. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J.

In some embodiments, tartar control agent is present at a concentration of from about 0.01 to 10%, by weight. In some embodiments, the tartar control agent is present at a concentration of about 1%, by weight. In some embodiments, sodium phosphate monobasic is present at a concentration of from about 0.01 to about 5%, by weight. In some embodiments, sodium phosphate monobasic is present at a concentration of about 1%, by weight. In some embodiments, disodium phosphate is present at a concentration of from about 0.01 to about 5%, by weight. In some embodiments, disodium phosphate is present at a concentration of about 0.15%, by weight.

Other optional additives include antimicrobial (e.g., antibacterial) agents. Any orally acceptable antimicrobial agent can be used, including triclosan (5-chloro-2-(2,4-dichlorophenoxy)phenol); zinc and stannous ion sources; quaternary ammonium compounds such as cetylpyridinium chloride (CPC); bisguanides such as chlorhexidine; and benzalkonium chloride. A further illustrative list of useful antibacterial agents is provided in U.S. Pat. No. 5,776,435 to Gaffar, et al.

In some embodiments, antimicrobial agent is present at a concentration of from about 0.001 to about 1%, by weight. In some embodiments, the antimicrobial agent is cetylpyridinium chloride. In some embodiments, the cetylpyridinium chloride is present at a concentration of about 0.05%, by weight.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, saliva stimulating agent, useful for example in amelioration of dry mouth may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof. In some embodiments, a local or systemic analgesic such as aspirin, codeine, acetaminophen, sodium salicylate or triethanolamine salicylate can be used.

In some embodiments, the methods comprise the step of rinsing the oral cavity with a composition as described herein. In some embodiments, the shear thinning properties of the composition increase the flow and thus the area covered when agitated within the oral cavity. In some embodiments, a polymer film forms on the surface of the oral cavity following discharge of the composition which results in relief of dry mouth symptoms. In some embodiments, 5 ml or more of the composition is gargled. In some embodiments, 10 ml or more is used. In some embodiments, 10-50 ml is used. In some embodiments, 15-25 ml or more is used. In some embodiments, 15 ml or more is used. In some embodiments, the individual gargles with the composition multiple times per day. In some embodiments, the individual gargles with the composition on multiple days. In some embodiments, the individual gargles with the composition every 4 to 6 hours up to 6 times per day.

Embodiments of the present invention are further described in the following examples. The examples are merely illustrative and do not in any way limit the scope of the invention as described and claimed.

EXAMPLES

Example 1

Table 1 (below) describes the formulation of an exemplary composition of the present invention; and also provides concentration ranges for each of the ingredients.

TABLE 1

| Ingredient | % w/w | % w/w |
| --- | --- | --- |
| Water | 72.4 | 40-97 |
| Sorbitol | 10 | 1-25 |
| Glycerin | 7.5 | 1-25 |

TABLE 1-continued

| Ingredient | % w/w | % w/w |
| --- | --- | --- |
| Propylene glycol | 7 | 0.1-50 |
| Poloxomer 407 | 1 | 0.01-10 |
| Sodium phosphate monobasic | 1 | 0.01-5 |
| Sodium benzoate | 0.5 | 0.01-1 |
| Flavor | 0.2 | 0.01-1 |
| Disodium phosphate | 0.15 | 0.01-5 |
| Xanthan gum | 0.083 | 0.01-0.5 |
| Cellulose gum | 0.083 | 0.01-0.5 |
| Cetylpyridinium chloride | 0.05 | 0.001-1 |
| Carbomer | 0.05 | 0.01-0.5 |
| Sodium fluoride | 0.02 | — |
| Sodium saccharin | 0.01 | 0.001-0.5 |
| FD&C blue no. 1 | 0.000375 | — |

The compositions described in Table 1 (above) can be prepared by conventional methods known to those skilled in the art; however, one exemplary method of preparation is provided below.

Approximately ⅓ of the water content is added to a first vessel (Vessel 1), to which the Carbopol 971P is slowly added, with strong mixing. The remaining water content is added to a second vessel (Vessel 2), to which the Poloxomer 407 is added and mixed until fully dissolved. Sorbitol and glycerin are then added to Vessel 2. Sodium phosphate monobasic, sodium benzoate, anhydrous sodium phosphate dibasic, sodium saccharin and Betafin BP20 are then added to Vessel 2, each being added and mixed before the next is added. The cetylpyridinium chloride and dye are then added to Vessel 2, and then mixed for about 10 minutes to ensure that the entire batch is solubilized. Xanthan gum and carboxymethyl cellulose (CMC) are then slurried with propylene glycol. The mixture from Vessel 1 (Carbopol 971P and water) is then added to Vessel 2. The xanthan gum and CMC slurry is then added to Vessel 2 and mixed for about 15 minutes. Flavor is then added and mixed for about 5 minutes.

Example 2

This Example provides the ingredient listing for Comparative Example 1. Comparative Example 1 contains the following ingredients: water, xylitol, hydrogenated starch hydrolysate, propylene glycol, hydroxycellulose, aloe vera (Aloe Barbadensis) Leaf Juice, flavor, Poloxamer 407, calcium lactate, zinc gluconate, sodium benzoate, benzoic acid, potassium thiocyanate, and enzymes (Lactoferrin, Lysozyme, Lactoperoxidase, Glucose Oxydase).

Example 3

This Example provides the ingredient listing for Comparative Example 2. Comparative Example 2 contains the following ingredients: water, glycerin, sorbitol, poloxamer 338, PEG-60 hydrogenated castor oil, carboxymethylcellulose, cetylpyridinium chloride, copovidone, propylparaben, sodium benzoate, sodium phosphate, sodium saccharin, xanthan gum, and FD&C blue no. 1.

Example 4

This Example provides the ingredient listing for Comparative Example 3. Comparative Example 3 contains the following ingredients: water, glycerin, alcohol, propylene glycol, sorbitol, polysorbate 20, flavor, sodium benzoate, cetylpyridinium chloride, sodium saccharin, D&C yellow no. 10, and FD&C blue no. 1.

Example 5

This Example provides the ingredient listing for Comparative Example 4. Comparative Example 4 contains the following ingredients: water, glycerin, sorbitol, propylene glycol, poloxamer 407, monosodium phosphate, sodium benzoate, disodium phosphate, flavor, cetylpyridinium chloride, sodium fluoride, sodium saccharin, FD&C green no. 3, and FD&C yellow no. 5.

Example 6

This Example provides the ingredient listing for Comparative Example 5. Comparative Example 5 contains the following ingredients: water, sorbiotol solution, monosodium phosphate, poloxamer 338, flavor, potassium sorbate, phosphoric acid, sodium fluoride, polysorbate 20, FD&C blue no. 1.

Example 7

This Example provides the ingredient listing for Comparative Example 6. Comparative Example 6 contains the following ingredients: water, alcohol, benzoic acid, poloxamer 407, sodium benzoate, caramel color, eucalyptol, menthol, methyl salicylate, and thymol.

Example 8

This Example provides the ingredient listing for Comparative Example 7. Comparative Example 7 contains the following ingredients: calcium disodium EDTA, cetylpyridinium chloride, disodium phosphate, flavor, green 3, menthol, methyl salicylate, poloxamer 407, polysorbate 20, potassium sorbate, propylene glycol, sodium benzoate, sodium phosphate, sodium saccharin, sorbitol, water, yellow 5, and sodium fluoride.

Example 9

The viscoelastic, shear thinning behavior of an exemplary composition of the present invention was characterized using rheology, in a conventional stress-control rheometer using a cone and plate geometry. Typically, one of the rheological methods commonly used to characterize a solution as viscoelastic and shear thinning is a flow curve, which is a measure of the viscosity as a function of shear rate. Flow measurements were taken, in the shear rate range 0.1-100 sec$^{-1}$ for the various products analyzed here.

The shear thinning behavior can be quantified by fitting the flow curve to a power law function and looking at the Flow Rate Index ("n"). The flow rate index for a Newtonian fluid like water is 1, while for shear thinning fluids n<1. The Flow Rate Index of natural saliva is approximately 0.4.

Compositions of the present invention have a Flow Rate Index between 0.1 and 0.8, and preferably between 0.3 and 0.6. Additionally, the overall viscosity index, also called the consistency index ("k") is two orders of magnitude higher for compositions of the present invention than for Comparative Examples 1 and 2, or water. The combination of a Flow Rate Index less than 1 (preferably less than 0.85), and a Consistency Index greater than 10, allows compositions of the present invention to provide a unique mouthfeel—due, in part, to the deposition of the polymer film onto an oral surface—and superior dry mouth relief.

Table 2 (below) provides a comparison of the Flow Rate Indices and Consistency Indices of compositions of the present invention and commercially available mouthwash/rinse formulations (Comparative Examples 1 to 7). These variables are routinely used to quantify the flow behavior of Newtonian as well as viscoelastic fluids. The data described in Table 2, illustrates that the polymer systems of the present invention provide a shear thinning effect, like saliva, while the Comparative Examples behave as Newtonian fluids, much like water. Essentially, none of the Comparative Examples are shear thinning.

TABLE 2

| Composition | Flow Rate Index ("n") | Consistency Index ("k") |
|---|---|---|
| Water (Newtonian fluid) | 1 | 2.5 |
| Saliva (Viscoelastic) | 0.4 | 63.8 |
| Example 1 | 0.5 | 163.5 |
| Comparative Example 1 | 1 | 25.7 |
| Comparative Example 2 | 1 | 6.8 |
| Comparative Example 3 | 1 | 2.2 |
| Comparative Example 4 | 1 | 2.6 |
| Comparative Example 5 | 1 | 2.7 |
| Comparative Example 6 | 1 | 3 |
| Comparative Example 7 | 1 | 2.2 |

As those skilled in the art will appreciate, numerous changes and modifications may be made to the embodiments described herein without departing from the spirit of the invention. It is intended that all such variations fall within the scope of the appended claims.

What is claimed is:

1. An aqueous oral care composition comprising:
   from 0.07 to 0.09%, by weight, xanthan gum;
   from 0.07 to 0.09%, by weight, cellulose gum;
   from 0.04 to 0.06%, by weight, carbomer;
   from 0.001 to 1% by weight, cetyl pyridinium chloride; and
   an orally acceptable aqueous carrier;
   wherein the composition is a mouthwash or mouthrinse; and wherein the composition further comprises a humectant, and wherein the humectant comprises propylene glycol from 5 to 15% by weight, sorbitol from 5 to 25% by weight, and glycerin from 5 to 15% by weight; and wherein the composition has a G'/G" ratio of greater than or equal to 1; wherein G' is an elastic modulus and G" is a viscous modulus; and wherein the composition has a shear thinning effect, and wherein the composition is configured to coat the hard and soft tissue in the oral cavity so as to ameliorate the effects of dry mouth and wherein the composition does not comprise a saliva stimulating agent selected from the group consisting of citric, lactic, malic, succinic, ascorbic, adipic, fumaric and tartaric acids or combinations thereof.

2. The composition of claim 1, comprising:
   about 0.08%, by weight, xanthan gum;
   about 0.08%, by weight, cellulose gum; and
   about 0.05%, by weight, carbomer.

3. The composition of claim 1, further comprising an antibacterial agent.

4. The composition of claim 3, wherein said antibacterial agent is a zinc ion source.

5. The composition of claim 1, further comprising one or more components selected from a fluoride ion source; a tartar control agent; a buffering agent; an abrasive; and a combination of two or more thereof.

6. The composition of claim 5, wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

7. The composition of claim 1, wherein the orally acceptable aqueous carrier comprises greater than 40%, by weight, free water.

8. The composition of claim 1, further comprising one or more components selected from a fluoride ion source; a tartar control agent; a buffering agent; an abrasive; and a combination of two or more thereof.

9. The composition of claim 1, wherein one or more of water, Sorbitol, glycerin and propylene glycol comprise at least about 80%, by weight, of the composition.

10. A method of treating xerostomia comprising contacting an oral cavity surface of a subject in need thereof with the composition of claim 1.

* * * * *

UNITED STATES PATENT AND TRADEMARK OFFICE
CERTIFICATE OF CORRECTION

PATENT NO. : 10,449,139 B2  
APPLICATION NO. : 13/997381  
DATED : October 22, 2019  
INVENTOR(S) : Paloma Pimenta et al.

Page 1 of 1

It is certified that error appears in the above-identified patent and that said Letters Patent is hereby corrected as shown below:

On Page 2, under Item (56), "OTHER PUBLICATIONS", Line 11, delete "Rejjden" and insert -- Reijden --, therefor.

On Page 2, under Item (56), "OTHER PUBLICATIONS", Line 14, delete "Redden" and insert -- Reijden --, therefor.

Signed and Sealed this
Eleventh Day of February, 2020

Andrei Iancu
*Director of the United States Patent and Trademark Office*